(12) United States Patent
Hercules

(10) Patent No.: US 7,500,937 B2
(45) Date of Patent: *Mar. 10, 2009

(54) DIET COMPLIANCE SYSTEM

(76) Inventor: Jesse Thomas Hercules, 308 Wishing Tree La., Oxford, MS (US) 38655

( * ) Notice: Subject to any disclaimer, the term of this patent is extended or adjusted under 35 U.S.C. 154(b) by 208 days.

This patent is subject to a terminal disclaimer.

(21) Appl. No.: 11/308,020

(22) Filed: Mar. 3, 2006

(65) Prior Publication Data
US 2007/0208593 A1 Sep. 6, 2007

Related U.S. Application Data

(63) Continuation-in-part of application No. 11/164,911, filed on Dec. 9, 2005, now Pat. No. 7,172,530.

(51) Int. Cl.
*A63B 71/00* (2006.01)
(52) U.S. Cl. .............................. 482/4; 482/8; 600/300; 434/247
(58) Field of Classification Search ................. 434/247, 434/236; 128/921; 482/1–9, 900–902; 600/300, 600/595; 705/2
See application file for complete search history.

(56) References Cited

U.S. PATENT DOCUMENTS

| | | | |
|---|---|---|---|
| 4,796,182 A | 1/1989 | Duboff | |
| 4,924,389 A | 5/1990 | Gerbaulet et al. | |
| 5,673,691 A | 10/1997 | Abrams et al. | |
| 6,283,914 B1 | 9/2001 | Mansfield et al. | |
| 6,336,136 B1 * | 1/2002 | Harris | 709/219 |
| 6,513,532 B2 | 2/2003 | Mault et al. | |
| 6,607,483 B1 | 8/2003 | Holland | |
| 6,643,385 B1 | 11/2003 | Bravomalo | |
| 2004/0116780 A1 | 6/2004 | Brown | |
| 2005/0085343 A1 * | 4/2005 | Burrows et al. | 482/1 |
| 2005/0240444 A1 * | 10/2005 | Wooten et al. | 705/3 |

* cited by examiner

*Primary Examiner*—Glenn Richman
(74) *Attorney, Agent, or Firm*—Clausen Miller, PC (57) ABSTRACT

A computer-based system for monitoring and improving a user's dietary compliance by providing the user with multiple forms of feedback designed to encourage adherence to a dietary program. In one embodiment the system comprises a personal computer having a commercially available telephony card and a cellular telephone carried by the user. The system automatically calls the user each evening and prompts the user to input whether the user adhered to the dietary program for each of that day's meals. The system accepts and stores the input, calculates whether the user is achieving their dietary goal, and gives the user positive or negative audio feedback based on whether the user is meeting their dietary compliance target.

11 Claims, 5 Drawing Sheets

| User |
|---|

| UserFirstName | Jesse |
| UserLastName | Hercules |
| UserPhone1 | 2340475 |
| UserPhone2 | 8160286 |
| UserTarget | 75 |
| UserActual | 73 |
| CallTime | 4:00PM |

[Stop Calling User]
[Start Calling User]

UserTarget is the user's target percentage adherence to the diet plan. For example, UserTarget of 90 means the user's target is to eat 90% of meals according to the diet UserActual is formatted identically to UserTarget, but it is the user's self-reported actual adherence over the last 30 days. You cannot change it here.

CallTime is the time each day the user wishes to be called by the system. You must click "Start Calling User" before the calls will begin. The system will call each day for 365 days.

Clicking "Stop Calling User" stops all future calls but preserves all past data. If the user re-starts the program, use "Start Calling User" rather than entering the same user twice.

Record: |◄| ◄ | 1 | ► | ►| |►*| of 1

Jesse

DIET COMPLIANCE SYSTEM

CROSS REFERENCE TO RELATED APPLICATION

This is a continuation-in-part of pending application Ser. No. 11/164,911 filed Dec. 9, 2005.

FIELD OF THE INVENTION

This patent relates to the field of exercise and diet compliance monitoring systems. More particularly, this patent relates to a system and apparatus for monitoring and improving a user's exercise or diet compliance by providing the user with multiple forms of feedback designed to encourage adherence to an exercise schedule or diet regimen.

DESCRIPTION OF THE RELATED ART

Long-term consistent adherence to an exercise schedule or diet regimen is difficult for persons to achieve. This is true even when persons recognize and desire the health benefits that come from regular exercise and diet. There are a number of reasons why people find consistent adherence difficult.

The main problem with current diet monitoring systems is that people, over the long term, will not use a system with heavy data-entry and bookkeeping requirements. Some systems require the user to use branching lists to select each item of food. Example: selecting Fruit->Apple->Large enters a large apple into your daily food eaten. It becomes quite tiresome to do this over thirty or more items eaten each day. Also, lots of things we eat—like an Applebee's Teriyaki Chicken Bowl—don't fall easily into these categories.

Other systems make data entry simpler by asking only for calorie counts, or for grams of fat, protein, and carbohydrates in each meal. But these systems just shift the work onto the user to determine and keep track of calories or fat grams in each thing they eat.

People don't and won't use these kinds of systems over the long term. Thus there is a need for a diet compliance system that uses compliance data rather than food data. In other words, a system that just asks whether the user's meal was 'on-program' (ie, compliant) or not.

Many dieters buy a diet book (eg, "The South Beach Diet™"), buy pre-made meals (eg, Jenny Craig™), or join a diet group (eg, Weight Watchers™). These systems do a good job of teaching people what an appropriate meal is. Dieters can tell you whether their last meal was compliant or not. But these approaches all share two compliance problems that the present invention solves.

The first problem is the 'all or nothing' compliance problem. Dieters are often very motivated and have extremely high compliance rates at the start of their diet program. Then external pressures often cause them to eat a few noncompliant meals in a row. Objectively, the dieter is still perhaps 85% compliant and has enjoyed significant weight loss. Subjectively, the dieter may consider the diet a failure at this point and spend the next month being noncompliant. Later, the dieter may get motivated and start the compliant-noncompliant cycle again. The present invention breaks this cycle by giving the dieter her objective statistics on a 30-day rolling basis and telling her how many compliant meals are needed to get back to her target (e.g., 90%) goal.

The second problem is the 'post-diet weight gain problem'. The dieter reaches a target weight, switches from dieting to his previous overeating habits and regains the weight. The present invention solves this problem. The user may need a 90% or better target compliance to lose weight, but the user can scale back to a 75% or so target to maintain his target weight. So the user is able to eat out at restaurants and/or eat like everyone else at a few social occasions a week. But, since the user eats strictly-compliant meals the other 75% of the time, he is able to maintain a healthy weight.

Conventional post-diet advice usually has been to scale up each meal to a 'regular' instead of a 'diet' meal. But in practice, dieters are not able to take every diet meal and scale up, say, 30%. But with the present system the dieter can eat a preset percentage of 'compliant' and 'non-compliant' meals each week and effectively accomplish a similar "scale up." Because the present system actively prompts the user for input, and keeps track of the user's compliance statistics automatically, the user accomplishes this 'scale up' without impractical manual bookkeeping.

Various systems that monitor a user's dietary intake, caloric expenditure and/or exercise level and provide feedback regarding the user's progress toward a goal are known in the art. Some of them are described below.

Duboff U.S. Pat. No. 4,796,182 describes a device for enabling a dieter to electronically track his or her progress by entering into the device the units consumed of each type of food. The device then subtracts that number of units from the dieter's daily allowance and calculates the units remaining for that day. The device can provide negative reinforcement by indicating when the daily or weekly allowable units have been exceeded. Unlike the present invention, the device does not prompt the user for input, and requires the user to input data for each item of food eaten.

Gerbaulet et al. U.S. Pat. No. 4,924,389 describes a device that enables a user to keep track of calories consumed and compare that total to a daily recommended quantity. Nine categories of food are assigned a particular calorie value. The user weighs the food to be consumed in each category and the device calculates the total caloric content of the food to be consumed. The device can indicate a dietary imbalance when, for example, the user is not eating enough food of a particular category. The device can also indicate whether the user has exceeded that day's allowable caloric intake. Lights tell the user whether he has eaten too few or too many meals in a given day. Unlike the present invention, the device does not prompt the user for input, and requires the user to input data for each item of food eaten.

Abrams et al. U.S. Pat. No. 5,673,691 discloses a hand held device that helps a user meet his or her exercise and/or dietary goals by applying behavior modification techniques. The device tracks the user's exercise and eating, determines the user's average daily caloric intake and expenditure, and tracks the user's weight to determine weekly weight loss. The device determines how the user is doing compared to his own dietary goals and provides positive feedback in the form of a message or a weight loss graph. Unlike the present invention, the device does not prompt the user to enter dietary compliance information each day. Also unlike the present invention, the device requires detailed dietary input including each item of food eaten.

Mansfield et al. U.S. Pat. No. 6,283,914 discloses a device that uses barcode technology for enabling a dieter to control calorie intake by determining when calorie limits have been reached in relation to a diet plan. To use, the user scans in the food item bar code to identity the food item and inputs serving size information using a turning set-wheel. The device then calculates the caloric intake of the food item and determines whether the item fits within the dieter's goal. If so, and if the product is eaten, the user confirms the choice by pressing a switch. The device then gives a running total of the day's caloric consumption and compares it to the user's dietary goal. The device can display in bar graph form whether the dieter is meeting his or her daily goal. Unlike the present invention the device does not notify the user that it is time for an entry, and requires data entry for each item of food eaten.

Mault et al. U.S. Pat. No. 6,513,532 discloses a combination diet and activity monitoring device. The diet portion of the device allows the user to indicate when the dieter has eaten food and the food eaten. The device can use this information to determine caloric intake. Unlike the present invention, the device does not notify the user that it is time for making an entry or calculate percent compliance with a diet plan.

Holland U.S. Pat. No. 6,607,483 discloses a hand held fitness monitoring system that can keep track of the physiological data, workout data and dietary data for a group of "members" participating in a fitness program. The system provides positive feedback by enabling a trainer to monitor changes in a member's physiological data so that the member can be informed of any progress.

Brown U.S. Publication No. 2004/0116780 A1 discloses a system to enable a user to remotely measure his or her adherence to a diet program, select foods accordingly and have them delivered. The user uses input devices to enter into the system his or her physical characteristics (height, weight, etc.), and the system responds with a recommended dietary goal and a diet plan. If the user accepts the plan, the system generates a suggested grocery list. If the user accepts the list the system arranges to have the groceries delivered to the user.

Thus an object of the present invention is to provide diet system that avoids the 'excessive-data-entry' problem of other systems by requesting only yes or no responses to compliance queries.

Another object of the invention is to provide a diet system that automatically prompts the user for the compliance information.

Still another object of the present diet system is to reduce the dropout rates caused by the all-or-nothing problem.

Yet another object of the present diet system is to extend the revenue streams of conventional prepared meal and calorie counting diet programs. After the user reaches his target weight, he will continue subscribing to the present system to maintain his target weight. This provides subscription revenue as well as ongoing prepared-meal sales.

Further and additional objects will appear from the description, accompanying drawings, and appended claims.

SUMMARY OF THE INVENTION

The present invention is a computer-based system for monitoring and improving a user's diet compliance by providing the user with multiple forms of feedback designed to encourage adherence to the diet. The system "calls" the user at the end of each day and prompts the user to input whether they complied with their diet for their three daily meals. The system accepts and stores the input, calculates whether the user is achieving their dietary goal, and gives the user positive or negative feedback based on whether the user is meeting their dietary adherence target.

The system hardware requirements include a data processing device such as a personal computer, a video display monitor, and means for inputting data (such as a keyboard). The computer should have an internal telephony card for two-way remote communication, and the user should be equipped with a telephone communication device such as a cell phone for receiving messages from the system and for inputting data (such as dietary compliance) into the data processing device.

Software requirements include a database management program (such as Microsoft Access), and computer telephony application software.

The system works in the following manner. First, the user inputs into the computer his or her identification data and dietary goal (percentage of meals for which the user hopes to comply with her diet).

At a specified time at the end of each day the system queries the user whether he or she complied with the diet for the three meals eaten that day. The user inputs compliance information (typically a yes or no response for each meal) into the system using a telephone or other transmitting device. The system calculates the user's current percent compliance and notifies the user, providing positive reinforcement (if the user is meeting or exceeding their target goal) or negative reinforcement (if not).

DETAILED DESCRIPTION OF THE INVENTION

The present invention is a computer-based system for monitoring and improving a user's diet compliance by providing the user with multiple forms of feedback designed to encourage adherence to a diet regimen or program. The system "calls" the user at the end of each day and prompts the user to input whether they complied with the diet program for each of that day's meals. The system accepts and stores the input, calculates whether the user is achieving their dietary goal, and gives the user positive or negative feedback based on whether the user is meeting their dietary compliance target.

Hardware Requirements

Figure 1:
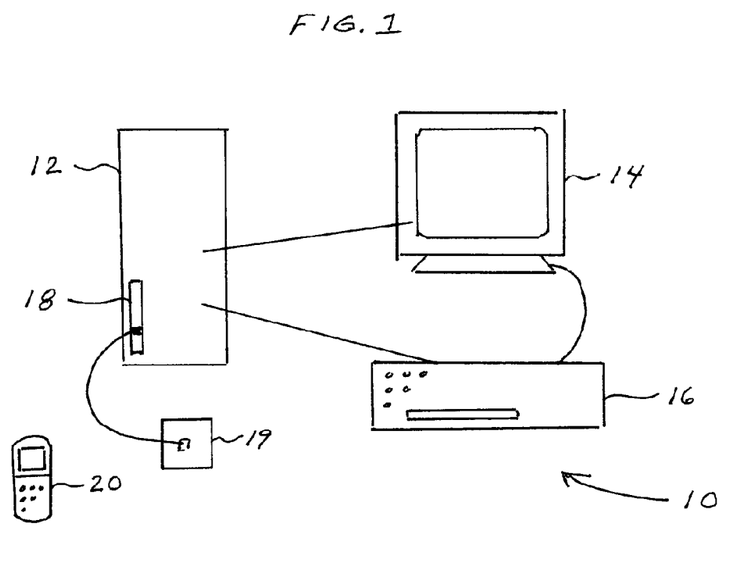
FIG. 1 is a schematic diagram of a diet monitoring system according to the present invention.

One embodiment of the present invention is shown schematically in FIG. 1. The system 10 hardware requirements include a data processing device 12 such as a personal computer having means for receiving and storing personal information and exercise compliance information about a user, including a user's dietary compliance goal, a video display monitor 14 and means for inputting data 16 (such as a keyboard). The computer 12 should have means for remotely contacting the user at the end of each day, such as an internal telephony card 18 wired to an analog phone port 19 for two-way remote communication, and processing means for calculating the user's new rate of compliance to their dietary program based on the compliance information inputted by the user, comparing that new rate of compliance to the user's compliance goal, and means for generating an appropriate feedback message and transmitting that message to the user.

In one embodiment, the computer 12 is a commercially available Hewlett-Packard Pavilion a630n desktop PC running the Windows XP operating system with an Intel Runtime License serial port plug. The computer 12 must include means for remote communication with the user, such as Intel's D41-JCTLS 4-port telephony card, if the means of communication is by telephone or two-way paging, or a standard ethernet card, if the means of communication is internet text messaging. If a telephony card is used, multiple phone lines per card and multiple cards per computer are possible.

The user should be equipped with a remote communication device 20 such as a cell phone for receiving messages from the computer 12 and for inputting data (such as dietary compliance) into the data processing device 12. Alternatively, the remote communication device can be a land line telephone, two-way pager, computer equipped with two-way internet text messaging capability, or any other suitable remote communication device.

The computer 12 may be any suitable data processing device, such as a commercially available Hewlett-Packard Pavilion a630n desktop PC running the Windows XP operating system with an Intel Runtime License serial port plug and an Intel D41-JCTLS 4-port telephony card installed. Multiple phone lines per card and multiple cards per computer are possible where the system involved multiple users (dieters). Alternatively, and for illustration purposes only, the computer 12 can be equipped with Voice Over Internet Protocol or two-way internet text messaging.

Software Requirements

Figure 2:
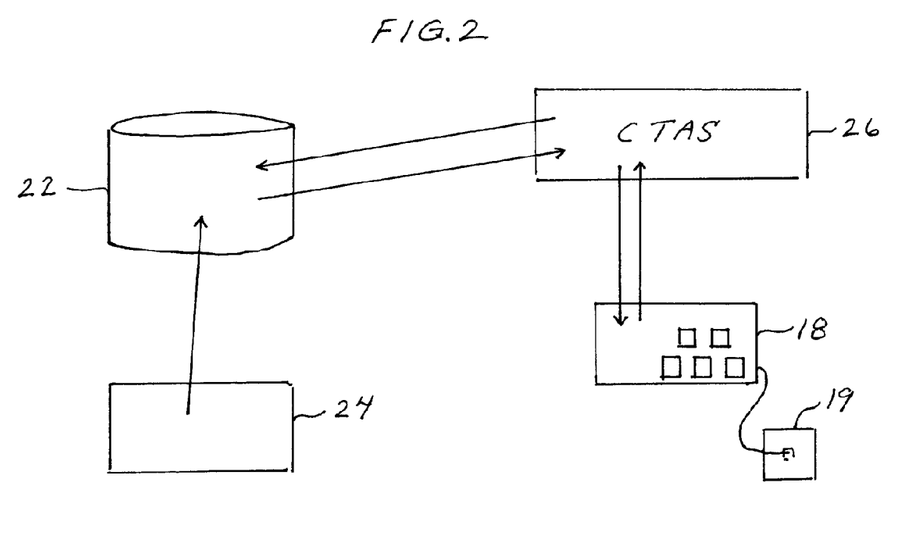
FIG. 2 is a schematic representation of the software requirements of the diet monitoring system of FIG. 1.

As shown in FIG. 2, software requirements include, for example, a database management program 22 (such as Microsoft Access 2003), forms software 24 (such as Microsoft Access Forms 2003 with VBA macros), and executable computer telephony application software (CTAS) 26. The application software 26 controls the telephony card 18, makes calls to the user, and takes the user's telephone input.

Alternatively, the software can include means to communicate with the user via internet text messaging rather than telephony.

The application software was written in the Intel Computer Telephony Application Development Environment (CTADE) using Intel's proprietary programming language and flow-charting tools. The CTADE includes a compiler which was used to compile the application and make it executable on a PC.

Figure 3:
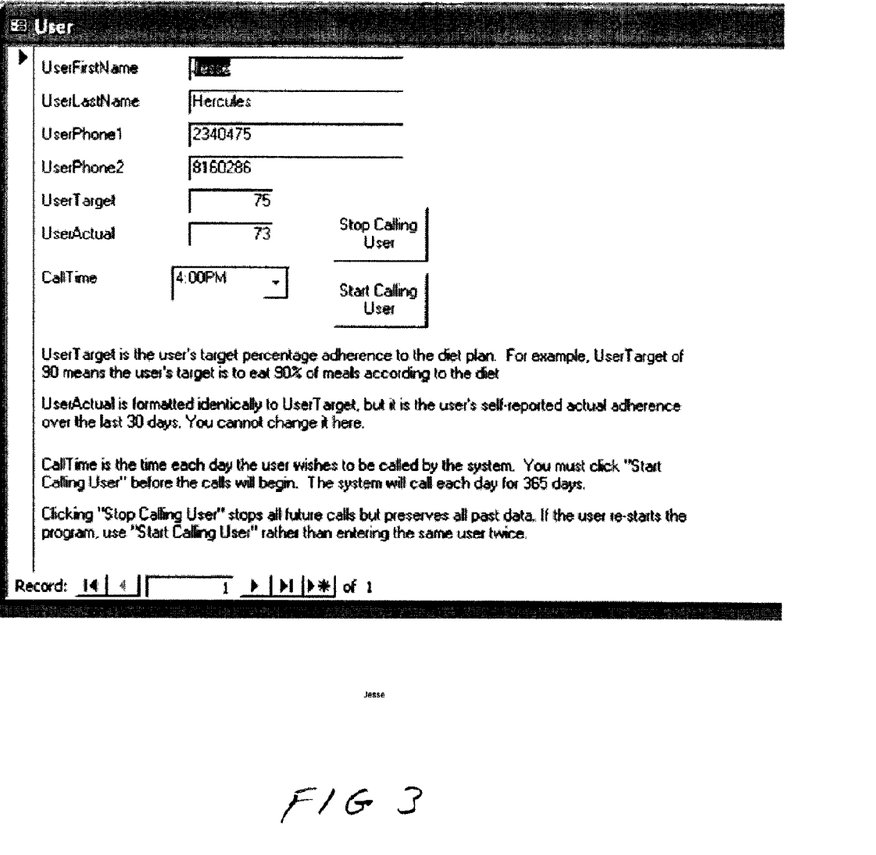
FIG. 3 is a sample user interface screen used in the diet monitoring system of FIG. 1.

The User Interface Page (FIG. 3) shows each user's contact information, target adherence percentage and actual adherence percentage. Actual adherence percentage is updated by the CTAS program during every call to a user.

Manner of Operation

User Information Input

The system 10 works in the following manner. First, using the user interface screen (FIG. 3), the user inputs into the computer 12 his or her identification and contact data (e.g. name and telephone number(s)), dietary goal (percentage of meals for which the user hopes to comply to his or her diet), and daily dietary prompt time ("Call Time").

Diet Inquiry and User Response

The system 10 can be used by multiple users at the same time. To accommodate multiple users, the database management program 22 runs in a continuous loop. At the beginning of the loop, the program 22 determines what call to make next. First, the program 22 looks in the database and finds the set of all calls it is to make. Then it sorts the calls in the order it will make them according to any suitable criteria, such as alphabetically by last name. The computer stores the ID of the user who is to be called first, then dials the user.

At the appropriate designated day and time, but typically each evening, the computer 12 queries the user (typically via telephonic communication) whether he or she complied with their diet for the three meals of that day. For each meal queried the user inputs his or her compliance information (typically a yes or no response in the form of a 1 or 2 on the telephone dial) into the computer 12 using a telephone or other telecommunication device 20.

If at any time when the user is prompted for input the user presses a key other than 1 or 2, the program can play a message that explains that only 1 or 2 is an appropriate response. The computer can then repeat the diet compliance inquiry.

If at any time when the user is being prompted for input the system does not "hear" the user input (caused, for example, by a bad telephone connection), the system gives the user three tries and then can move the prompt (inquiry) time one hour ahead of the current time and call back at that time.

If the user does not answer the telephone, the system can move the prompt time one hour ahead of the current time and call back at that time.

Calculation and Feedback

The computer 12 calculates the user's current percent compliance, typically for the last thirty days, and compares that percent to the user's target goal, and provides the user with feedback. The feedback may be positive reinforcement (if the user is meeting or exceeding their target goal) or negative reinforcement (if not). For example, if the user's actual diet adherence percentage is below target, the program can determine how many meals in a row for which the user must adhere to the diet to get back on target. (See Intervention Feature below). If the user is at or above the target percentage, the computer can play a positive verbal or musical message praising the user for being on track.

After going through this inquiry, calculation and feedback routine the computer program then starts its loop from the beginning.

In addition to the basic features described above, the system 10 can also have the following optional features:

Rolling Basis Feature

Unlike some previous compliance systems which can only handle a fixed start date, the present system 10 has the capability of handling a movable start date. With the "rolling basis" feature, the system software has the capability of calculating a new rate of dietary compliance based on a percentage of times the user has adhered to his or her diet during a previous predetermined number of days, rather than from a set start date. This feature keeps the focus on recent compliance because old meals—both compliant and non-compliant—drop out of the calculation as new ones are added.

Standing Start With Rolling Basis Feature

The computer software also has the capability of calculating a rate of compliance based on the percentage number of times a user has complied with his or her diet during the lesser of either a previous predetermined number of days or the number of days the user has used the system. This makes the compliance rate very sensitive to each episode of compliance at first, automatically transitioning to normal sensitivity as use continues. For example, if, after the first two days the user has complied with the diet only three of six times, the user's compliance rate will be 50 percent. Meeting dietary compliance for the next three meals the following day (and responding positively to the system's inquiry) will increase the compliance rate to 66 percent, a significant increase. However, as time goes on the compliance rate will be much less sensitive to the latest positive—or negative—result.

Intervention Feature

It can be useful psychologically for a user to know how quickly he or she can "get back on target", or increase his or her compliance to the set goal. To that end, the computer 12 may include means for calculating a number of meals after which the user will be next in compliance if the user responds positively to each future computer inquiry through the number of meals/days. The computer can provide both the date and the number of compliant meals needed to get back on target.

Non-optimized Target Feature

The program allows a user to set any dietary compliance goal, from 100% (optimized target) to anything less than 100% (non-optimized target). Thus a user can set a goal that is realistic and will provide real physiological benefits. This feature is also important in maintaining weight. A high target (e.g., 90%) may be needed to lose weight, but a substantially lower target (e.g., 75%) may be appropriate for maintaining weight over the long term.

EXAMPLE

In the example that follows, all text is spoken by a computer-generated voice. Plain text is spoken as shown, but where Boldface text is shown, the information is based on data in the database specific to that user. For example, the user's name and the user's compliance rate are in bold. Also, the bold text indicating the user "is" or "is not" meeting a target will change based upon that user's data.

When signing up for the service, the user selects a % adherence goal and a time each evening after dinner when they want to be called. The system also stores two or more phone numbers for the user along with the user's name.

Part I: Establishing the Phone Call (FIG. 4)

Figure 4:
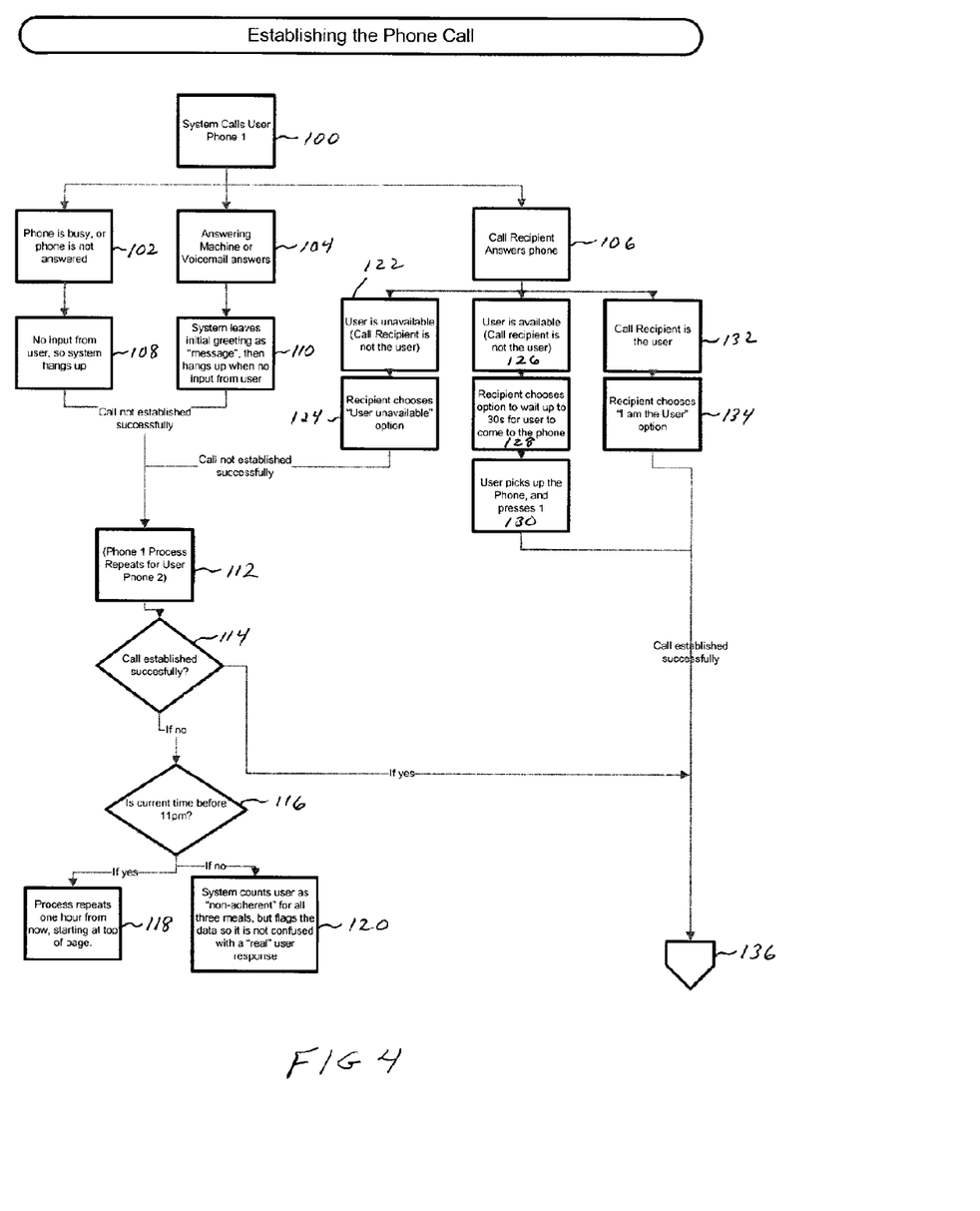
FIG. 4 is a flowchart for the establishing the phone call routine.

At the time specified by the user on the user interface screen (FIG. 3), the system calls the specified user inputted telephone number 1 (FIG. 4, Step 100). Either the phone is busy (Step 102), an answering machine answers (Step 104), or the user's phone rings (Step 106). If the phone is busy (Step 102) or an answering machine answers (Step 104) the system determines that the call cannot be established at that time and for that telephone number and tries user inputted telephone number 2 (Step 112). If the call still cannot be established successfully (Step 114), the system either initiates a call back procedure for one hour later (Step 118) or counts the user as non-adherent for all three meals that day (Step 120).

If the user's phone rings but the user is unavailable (Step 122), the recipient is prompted to choose the "User unavailable" option (Step 124).

If the user's phone rings and the user is available (Step 126), the recipient is asked to input a wait instruction (Steps 126-128):

System: Hello, this is the BE Lean system calling. Press one if you are Jesse Hercules. Press two if you want to wait for that person to come to the phone. Press three if that person is unavailable.

Call Recipient Presses 2

System: Please tell Jesse Hercules to press one when they answer the phone.

User comes to the Phone and Presses 1

Figure 5:
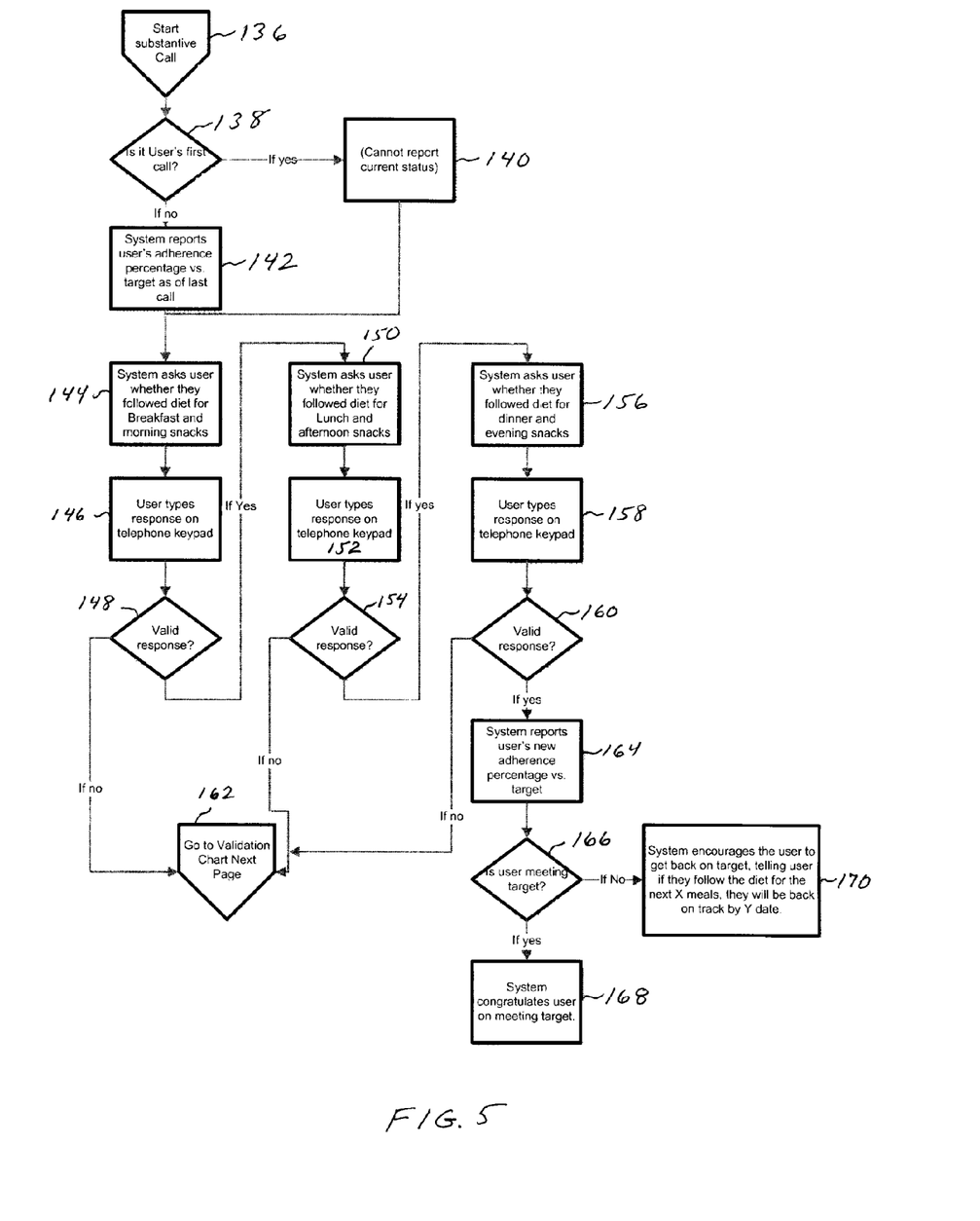
FIG. 5 is a flowchart for the substantive call routine.

Once the user picks up the phone and presses 1 (Step 130), the system initiates a substantive calling routine 136 (FIG. 5).

Part II: Substantive Calling Routine (FIG. 5)

The first step in the substantive calling routine is to determine if the call is the user's first call (Step 138). If not, the system initiates a reporting routine (Step 142) with sample dialog as follows:

System: Last time we talked, you had followed your program for 75 percent of your meals, and you were not meeting your target of 80 percent.

The system then initiates an inquiry routine for the three meals of that day (Step 144):

System: Did you follow the program this morning, including breakfast and snacks? Press one if you did, press two if you did not.

User presses 1 or 2 (Step 146)

System: Thank you. Did you follow your program this afternoon, including lunch and snacks? Press one if you did, press two if you did not.

User presses 1 or 2 (Step 152)

System: Thank you. Did you follow your program this evening, including dinner and snacks? Press one if you did, press two if you did not.

User presses 1 or 2 (Step 158)

After each meal inquiry the system determines whether the response was valid (Steps 148, 154, 160). If the response was not valid, the system initiates a validation routine (see Part III below). If the response was valid, then the system initiates a reporting routine (Steps 164-170) as follows:

System: Thank you. You have now followed your program for 88 percent of your meals for the past 30 days, and you are meeting your goal of 80 percent.

(If user is meeting target). Good job! Take a moment to enjoy the feeling of being on track to achieve your diet goals. (Step 168)

(If user is not meeting target). But don't give up. If you follow your diet for the next 5 meals, you will be back on target by Sep. 15, 2004. (Step 170)

Figure 6:
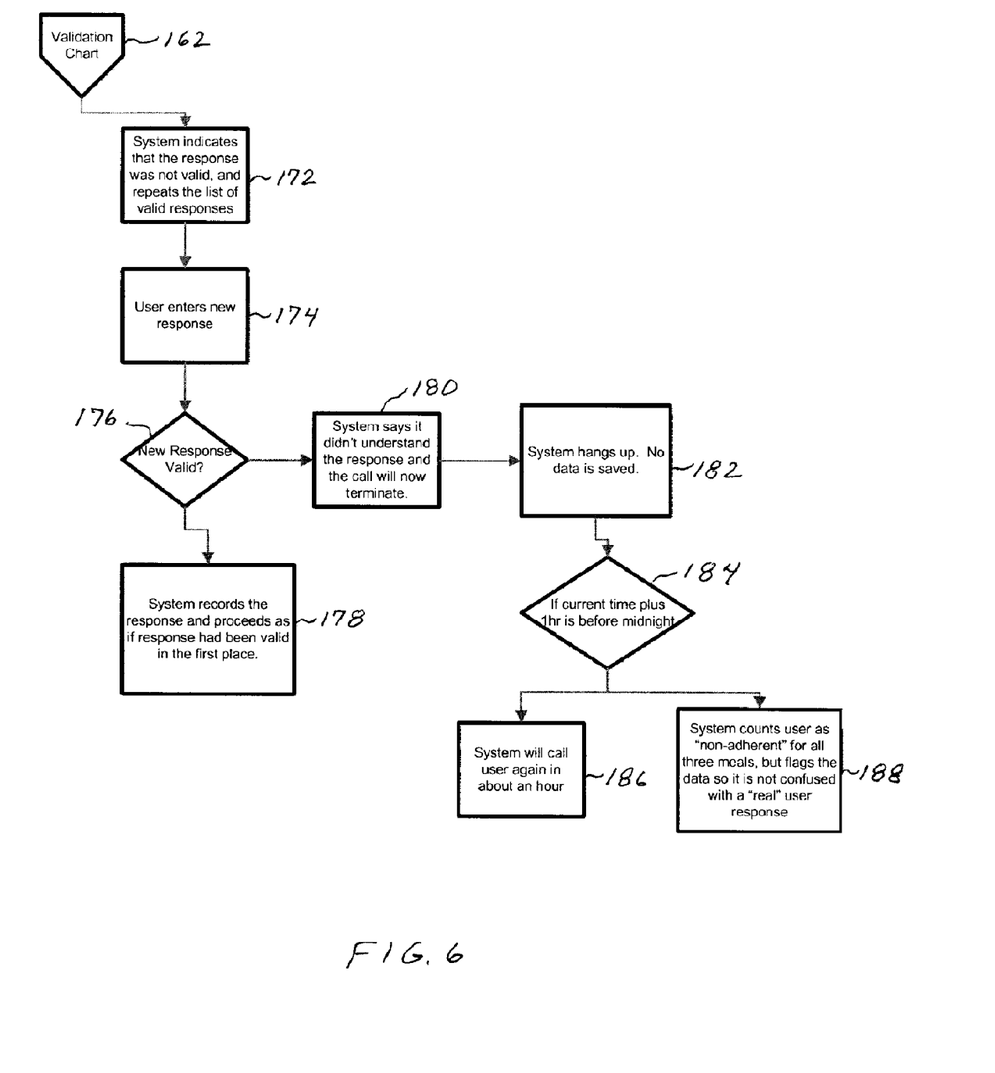
FIG. 6 is a flowchart for the validation routine.

Part III: Verification Script:

When the user is asked for input, there are a limited number of acceptable responses—usually a 1 or 2 are the only acceptable responses. However, the user may mistakenly press a 5, or the user may be unable to respond. Also, a bad phone connection—such as a cell phone nearly out of range—can cause a user response to go unheard by the system. If the user's response is not within the limited number of acceptable responses, the system goes through the following script (Steps 172-188):

System: You need to enter either [list of acceptable responses].

If user's new response is acceptable, the system continues as if the initial response had been acceptable.

If the user's new response is still unacceptable, the system goes through the following script:

System: Sorry, I didn't understand your response. This call will now terminate. (System then hangs up).

\* \* \*

It is understood that the embodiments of the invention described above are only particular examples which serve to illustrate the principles of the invention. Modifications and alternative embodiments of the invention are contemplated which do not depart from the scope of the invention as defined by the foregoing teachings and appended claims. For example, the system can be set up to inquire about more or less than three meals per day. The system can also be set up to inquire about dietary program compliance more or less than once per day. It is intended that the claims cover all such modifications and alternative embodiments that fall within their scope.

What is claimed is:

1. A computer-based system for monitoring and increasing a user's diet program compliance, the system comprising:

a computer having means for receiving and storing personal information about the user, including the user's name, telephone number and user-defined compliance goal; means for remotely and automatically contacting the user at least once per day and inquiring of a user's compliance for the three meals of that day; means for receiving and storing a user's compliance information in the form of a yes or no response for each meal; processing means for calculating a user's new rate of compliance to the dietary program based on the compliance information received remotely from the user, comparing that new rate of compliance to the user's compliance goal and automatically generating a feedback message; and means for automatically transmitting that feedback message to the user; and remote means by which the user can receive from the computer a compliance inquiry, input to the computer the user's compliance information, and receive from the computer the feedback message.

2. The computer-based system of claim 1 wherein the remote means comprise a cell phone.

3. The computer-based compliance system of claim 1 wherein the user's compliance goal is less than 100%.

4. The computer-based system of claim 1 wherein the new rate of compliance to the diet program is calculated as the percentage of times the user has adhered to the diet during the previous predetermined number of meals or days.

5. The computer-based system of claim 1 wherein the new rate of compliance is calculated as the percentage of times the user has adhered to the diet during the lesser of either the previous predetermined number of days or the number of days the user has used the computer-based system.

6. The computer-based system of claim 1 wherein the processing means includes means for calculating a date when the user will be next in compliance if the user adheres to the diet for each future meal through said date and wherein the feedback message includes said date.

7. A method of monitoring and increasing the compliance of a user following a dietary program, the method comprising the steps of:

the user inputting into a computer system a user's identification and contact data and a dietary compliance goal;

at a predetermined time each day the computer system automatically requesting the user to input into the computer system whether the user did or did not adhere to the dietary program for each of that day's meals;

the user entering a yes or no response into the computer system via a remote device;

the computer system calculating the percentage of times the user has adhered to the dietary program and comparing that percentage compliance to the user's dietary compliance goal; and the computer system providing the user with remote feedback regarding whether the user is currently in compliance with the user's dietary compliance goal.

8. The method of claim 7 wherein during the calculating step the computer calculates a percentage of times the user has adhered to the diet during a previous predetermined number of days.

9. The method of claim 7 wherein during the calculating step the computer calculates a percentage of times the user has adhered to the dietary program during the lesser of either a previous predetermined number of days or a number of days the user has followed the dietary program.

10. The method of claims 8 or 9 wherein during the calculating step the computer calculates a date when the user will next be in compliance if the user adheres to the dietary program for each future meal through said date and wherein, during the providing step, the computer provides the user feedback identifying said date.

11. The method of claim 7 wherein the feedback message includes the new rate of compliance.

* * * * *